United States Patent [19]

McIntyre

[11] Patent Number: 5,291,895
[45] Date of Patent: Mar. 8, 1994

[54] EVALUATION OF HEART MECHANICAL PERFORMANCE

[76] Inventor: Kevin M. McIntyre, 160 Commonwealth Ave., Boston, Mass. 02116

[21] Appl. No.: 998,410

[22] Filed: Dec. 29, 1992

Related U.S. Application Data

[63] Continuation of Ser. No. 758,783, Sep. 12, 1991, abandoned, which is a continuation of Ser. No. 563,869, Aug. 7, 1990, abandoned, which is a continuation of Ser. No. 353,373, May 16, 1989, abandoned, which is a continuation of Ser. No. 125,561, Nov. 25, 1987, abandoned, which is a continuation of Ser. No. 740,524, Jun. 3, 1985, abandoned.

[51] Int. Cl.⁵ .............................................. A61B 5/02
[52] U.S. Cl. ................................... 128/672; 128/677; 128/687
[58] Field of Search ................... 128/670–672, 128/677–681, 686, 687–690, 716, 725–730

[56] References Cited

PUBLICATIONS

"A Noninvasive Method of Predicting Pulmonary-Capillary Wedge Pressure," K. M. McIntyre, J. A. Vita, C. T. Lambrew, J. Freeman, and J. Loscalzo, Dec. 10, 1992, pp. 1715–1720, The New England Journal of Medicine Richard Gorlin, M.D., Dec. 10, 1992, The Mount Sinai Medical Center.

*Primary Examiner*—Lee S. Cohen
*Assistant Examiner*—John P. Lacyk
*Attorney, Agent, or Firm*—Fish & Richardson

[57] ABSTRACT

The invention evaluates the mechanical condition of a heart in a patient by noninvasively providing a pulse signal representative of arterial pulsation by placing a transducer sufficiently close to the skin of the patient to provide an electric signal representative of the arterial pulsation. The patient is subjected to a heart-straining maneuver to provide an arterial pulse contour square-wave signal during the heart-straining maneuver having an early strain phase amplitude at the beginning of the heart-straining maneuver and a later strain amplitude at the end of the heart-straining maneuver. An indication is provided of the ratio of the late strain phase amplitude which ratio is representative of the mechanical condition of the heart of the patient. The invention may also provide an indication of the relationship between that ratio and the pulmonary capillary wedge pressure of the patient. The invention may also provide an indication of the state of hydration of the patient.

18 Claims, 13 Drawing Sheets

| PULSE | HEART | PULSE RATE |
|---|---|---|
| 4 | .45 | 101 |
| 3 | .45 | 102 |
| 2 | .39 | 103 |
| 1 | .36 | 107 |
| END OF MANOEUVRE | | |
| 0 | .24 | 27 |
| 1 | .42 | 108 |
| 2 | .45 | 113 |
| 3 | .64 | 115 |
| 4 | .91 | 117 |
| 5 | 1.27 | 116 |
| 6 | 1.61 | 104 |
| 7 | 1.70 | 69 |
| 8 | 1.53 | 69 |
| 9 | 1.55 | 69 |
| 10 | 1.67 | 67 |
| 11 | 1.61 | 62 |
| 12 | 1.42 | 57 |
| 13 | 1.21 | 56 |
| 14 | 1.18 | 58 |
| 15 | 1.24 | 58 |

B/A ≅ 1.0: HEART FAILURE / PCWP = α 20mmHg

B/A ≅ 0.7: LESS SEVERE HEART FAILURE / PCWP ≅ 16mmHg

B/A ≅ 0.3: NORMAL STATIC / PCWP ≅ 10mmHg

B/A ≅ 0.15: HYPOVOLEMIA / PCWP ≅ 4-5mmHg / (DEHYDRATION)

NOTE: VERY RAPID DOWNSLOPE OF "STRAIN PHASE" CURVE

EVALUATION OF HEART MECHANICAL PERFORMANCE

There is a microfiche appendix consisting of three microfiche with 203 frames.

This application is a continuing application of application Ser. No. 07/758,783 filed Sep. 12, 1991, now abandoned; which is a continuing application of application Ser. No. 7/563,869 filed Aug. 7, 1990 now abandoned; which is a continuing application of application Ser. No. 07/353,373 filed May 16, 1989 now abandoned; which is a continuing application of application Ser. No. 07/125,561 filed Nov. 25, 1987 now abandoned; which is a continuing application of application Ser. No. 06/740,524 filed Jun. 3, 1985 now abandoned, the whole of which are hereby incorporated by reference.

The present invention relates in general to evaluating the mechanical performance of the heart, and more particularly concerns novel apparatus and techniques for making this evaluation with relatively inexpensive apparatus. This apparatus is relatively easy to operate by relatively unskilled personnel to achieve reliable results. The system can be adapted to be suitable for use in the office of an individual medical practitioner, or other medical or non-medical locations using noninvasive techniques. Such techniques offer no discomfort to the patient being evaluated, while providing a reliable indication of mechanical heart pumping performance

BACKGROUND OF THE INVENTION

The present invention represents an improvement of the invention disclosed in U.S. Pat. No. 3,776,221 granted Dec. 4, 1973, to Dr. Kevin M. McIntyre, Esq. entitled DETECTING IMPAIRED HEART MECHANICAL PERFORMANCE AND APPARATUS THEREFORE. This patent discloses establishing the time derivative of the systemic arterial pulse pressure at a control level in the subject patient. The patient performs a straining maneuver, such as a Valsalva maneuver, while the time derivative of the systemic arterial pulse pressure signal is recorded. Preferably, the systemic arterial pulse pressure, mean pressure, heart rate and left ventricular ejection time are also established, and can be interpreted so that the presence or absence of impairment in the performance of the left ventricle can be detected.

It is an important object of this invention to provide improved apparatus and techniques for evaluating mechanical heart performance.

SUMMARY OF THE INVENTION

According to the invention, there is provided an apparatus having transducing means for noninvasive placement near the skin of a patient for providing an electrical pulse signal representative of systemic arterial pulse pressure and pressure applying means, such as an inflatable cuff, for applying pressure through the transducing means for establishing pressure on the skin adjacent the transducing means within the range of substantially above diastolic pressure to half diastolic pressure. I have found that comparison of measurements obtained in this pressure range, especially at pressures substantially above diastolic, provides increased information compared to use of pressures outside this range. There is preferably a pressure source coupled to the pressure applying means for providing pressure to the latter. There is means for displaying a pulse signal characteristic of the electrical pulse signal which in turn reflects the arterial systolic signal, preferably displaying an indication of an aspect of each pulse beat and an indication of the time interval between consecutive pulse beats. There is preferably expiration means for receiving expired air from a patient to be evaluated comprising a confined volume with a small aperture for releasing the expired air and pressure sensing means coupled to the confined volume for providing an electrical air pressure signal representative of the pressure established in the confined volume by the expiring patient. Preferably, there is display means for providing an indication of the air pressure signal as a function of time.

According to a method of the invention, the transducing means is placed adjacent the skin, preferably against a digit. Pressure is applied to the skin at least in part through the transducing means, preferably with an inflatable cuff surrounding the digit and transducing means. Preferably, there is a pressure source coupled to the cuff, such as a sphygmomanometer bulb coupled through a hose including a valve that may be closed when a desired pressure is reached, typically determined by observing a pressure indicator, to establish a base level of the pulse signal.

In some preferred embodiments, the patient is subject to a heart straining maneuver. In one maneuver, termed, Valsalva, the patient blows into the expiration means until the pressure indicating means indicates air pressure in the confined volume within a predetermined range, typically 30 to 50 mm of mercury, for a predetermined time interval, typically 8 to 20 seconds, during this straining maneuver, such as phases I and II of a Valsalva maneuver. The patient then breathes normally while the transduced pulse signals are recorded during phases III and IV of a Valsalva maneuver and response for a brief period thereafter. The signals may be processed to provide an indication of one or more of the heart rate, pressure or displacement time derivative of the pressure or displacement signal, integral of the pressure or displacement signal, peak pressure, mean pressure and diastolic pressure, and times to the occurrence of certain events, such as time to maximum and minimum signal amplitudes, and impulse rates, as they occur in the course of Valsalva maneuver, and the response to it, and other interventions, alone, or in combination. One or more of a display of these signals for the four phases of the Valsalva maneuver may be observed to determine an evaluation of the mechanical performance of the heart. An alternative maneuver is the Mueller maneuver, where the patient inhales to create a negative pressure on the chest.

In other preferred embodiments the method further comprises the step of subjecting the patient to a second and also a third heart straining maneuver; the heart straining maneuver is principally a Valsalva maneuver or a Mueller maneuver but may be other maneuvers or interventions, alone or in combination including, a handgrip exercise, or other exercise, causing the patient to change position (lie supine, stand, etc.), causing the patient to raise his/her legs, immersing one arm of the patient in ice water, subjecting the patient to psychological stress, such as solving mathematical problems, administering a drug to the patient, performing balloon angioplasty or performing coronary artery bypass grafting; most preferably the drug is chosen from a nitrate, a calcium channel blocker or a B-adrenergic receptor blocker, and a second or third or other maneuvers are after the detecting step and the method further comprises detecting the change in pulse signal after the second or third or other maneuvers relative to the pulse signal during a base period during, a base, before the second, third or subsequent maneuvers.

In another method of the invention, the mechanical condition of the heart is evaluated by noninvasively providing a pulse signal representative of arterial pulsation by placing pressure sensitive transducing means, for providing an electrical signal representative of pressure, in contact with the skin of a patient while applying pressure at least in part through the pressure sensitive transducing means to adjacent skin at a controlled pressure within the range of substantially just above the diastolic pressure of the patient and a pressure of substantially half of the diastolic pressure, without subjecting the patient, whose blood pressure is being characterized by the pulse signal, to a heart straining maneuver, and detecting the pulse signal, or subjecting the patient to maneuvers other than the breathing maneuvers, such as isometric exercise.

According to another feature of the invention, the pressure sensitive transducing means may comprise a plurality of transducers at a corresponding plurality of skin locations, such as different fingers, at a corresponding plurality of controlled pressures.

Numerous other features, objects and advantages of the invention will become apparent from the following detailed description when read in connection with the accompanying drawings in which:

BRIEF DESCRIPTION OF THE DRAWINGS

FIG. 10 shows the change in display in a patient with abnormal response to the Valsalva maneuver alone (A), with handgrip exercise (B) and with the patient supine (C); FIG. 11 shows the change in display in a patient with abnormal response to Valsalva maneuver alone (A), repeated Valsalva maneuver (B), handgrip exercise (C), and with the patient supine (D); FIG. 12 shows the change in display in a patient with nearly normal response to Valsalva maneuver alone (A), with the patient supine and legs elevated (B), and with the patient supine, with legs elevated and with handgrip exercise (C); FIG. 13 shows the change in display in a patient with abnormal response to Valsalva maneuver thought to be due to an abnormality of growth in the muscle of the heart (A), and five days after treatment with Verapamil, which improves the abnormal condition, followed by the Valsalva maneuver (B); FIG. 14 shows the change in display in an almost normal response to Valsalva maneuver alone (A), with handgrip exercise (B) and with the patient supine, with legs elevated (C); FIG. 15 shows the change in display in a patient with normal response to Valsalva maneuver (A), after repeated Valsalva maneuver (B) and handgrip exercise (C); FIG. 16 shows the change in response in a patient with almost normal response to Valsalva maneuver (A), and after repeated Valsalva maneuvers (B, C, D); FIG. 17 shows the change in display in a patient with nearly normal response to Valsalva maneuver (A, B) with handgrip exercise (C) and with the patient supine (D);

DESCRIPTION OF THE PREFERRED EMBODIMENTS

Figure 1:
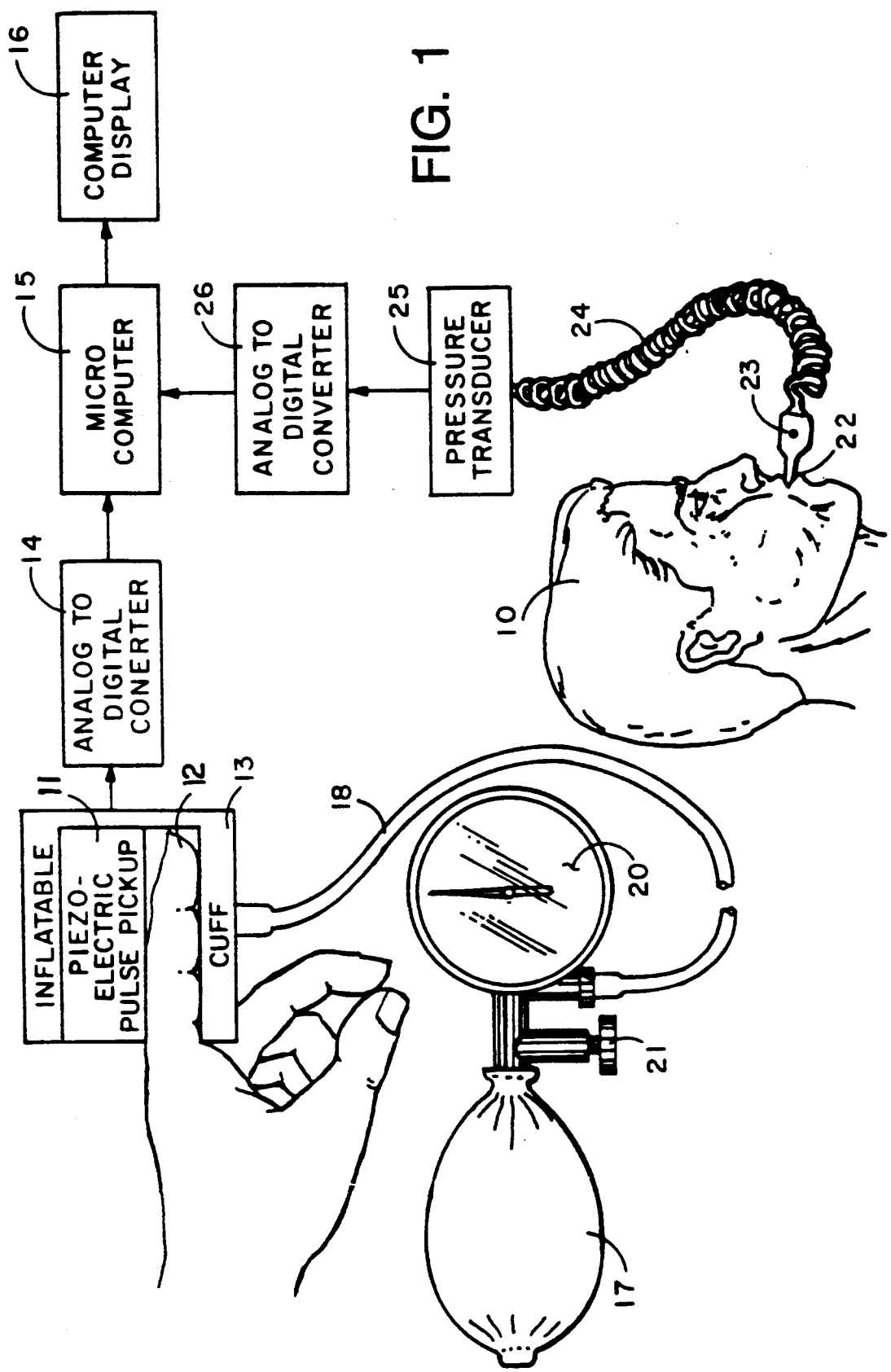
FIG. 1 is a combined pictorial-block diagram illustrating the logical arrangement of a system according to the invention.

With reference now to the drawings and more particularly FIG. 1 thereof, there is shown a combined pictorial-block diagram illustrating the logical arrangement of a system according to the invention. A patient 10 to be evaluated places a finger 11 between piezoelectric pulse pickup 12 and inflatable cuff 13 to provide a pulse signal converted by analog to digital converter 14 to digital form that is processed by microcomputer 15 to provide on display 16 representation of the pulse sensed by pickup 12. The finger pickup may be positioned at the tip of the finger or at some more proximal or lateral point. It may also be positioned at other areas of a body where arteries are close to the skin. Pressure source 17, typically a sphygmomanometer bulb connected to cuff 13 through hose 18 having a valve 21 for closing hose 18 when inflatable cuff 13 is inflated, applies pressure at least in part through piezoelectric pulse pickup 12 to the skin of finger 11 surrounded by cuff 13. Pressure indicator 20 indicates the pressure, preferably substantially the diastolic pressure or substantially above the diastolic pressure (e.g., up to 4 times diastolic) of patient 10. The diastolic pressure for the patient may be determined by taking the patient's blood pressure in a conventional manner. Alternatively, the pressure may be taken automatically by an appropriate device so that the blood pressure level can be recorded continuously by the computer, and so that the pressurizer pressure (13) can be set or changed automatically to provide a desired relationship to the patient's actual blood pressure.

Figure 5:
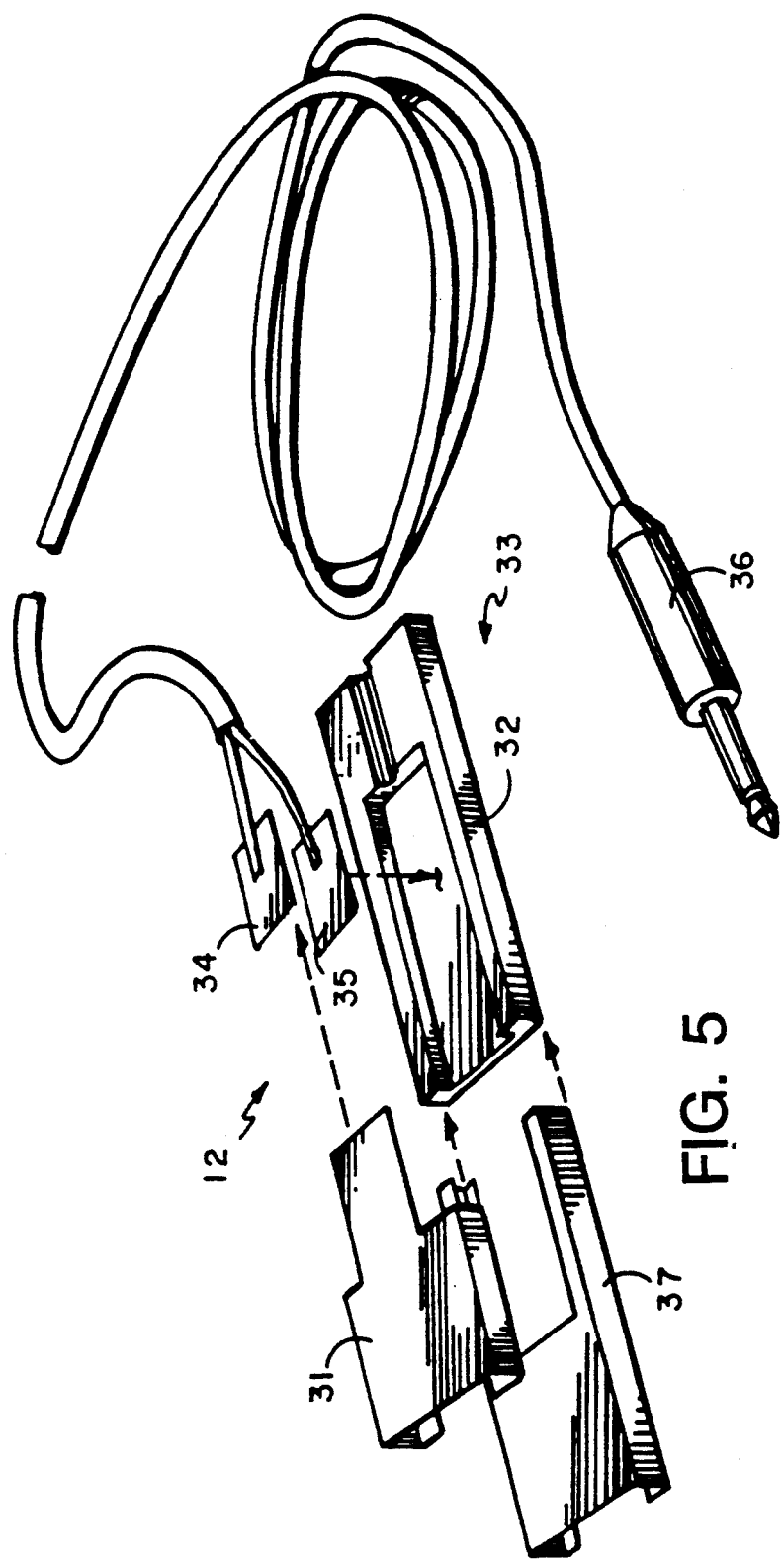
FIG. 5 is an exploded view of an exemplary embodiment of a transducing assembly for pulse detecting.

Referring to FIG. 5, there is shown an exploded view of an exemplary pulse pickup assembly 12 for use according to the invention. A piezoelectric crystal (Ceramic on Brass, Murutta/ERI, Future Electronics, Marlborough, Mass.) 31 is placed across legs 32 of holder 33 and contacted on opposite sides by a pair of leads 34, 35 brought out to a miniature phono plug 36 that may plug into analog-to- digital converter 14 (FIG. 1). A ground shield 37 completes the assembly. While FIG. 5 shows the pickup assembly of generally rectangular form, pickups of other shapes may be used, for example, pickups with a circular opening in the tip exposing a circular piezoelectric membrane surface, and pickups shaped for circumferential sensing or multiple pickups in the same pressurizer chamber. Membrane 31 is typically a commercially available polymer.

Figure 6:
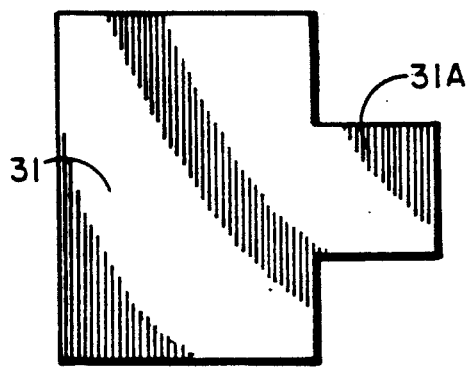
FIG. 6 is a plan view of a portion of a metal backed piezoelectric film.
Figure 7:
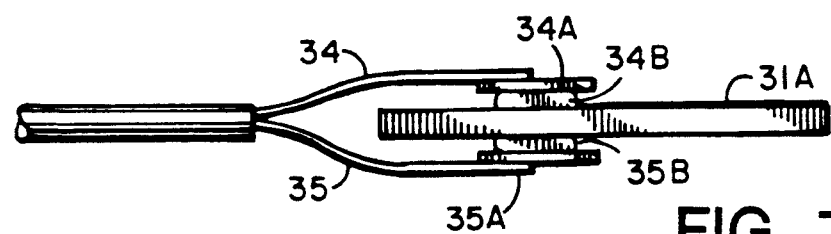
FIG. 7 is a side view partially in section illustrating connections to the piezoelectric film.

Referring to FIG. 6, there is shown a fragmentary plan view of the end portion of membrane 31 including step 31A to which the contacts are attached. Referring to FIG. 7, there is shown a side fragmentary view illustrating the detail for connection to step 31A. Leads 34 and 35 are soldered or otherwise attached to metal buttons 34A and 35A, respectively, which are connected to opposite sides of tab 31A by dabs of conductive epoxy 34B and 35B, respectively.

Specific components of the system are known in the art. The techniques for using a microcomputer to provide a representation of the peak pressure of each pulse and the pulse are well within the skill of a person having ordinary skill in the computer art and are not described in detail herein to avoid obscuring the principles of the invention. In a specific embodiment of the invention, microcomputer 15 (FIG. 1) was an IBM Compatible with an associated picture tube display. The steps in a suitable program are set forth in the microfiche appendix.

The blood pressure may be determined by the standard cuff-sphygmomanometer method or by an automatic system, such as the Doppler technique, or any other technique for providing an indication of blood pressure.

Having described the system arrangement, its mode of operation will be described. Patient 10 (FIG. 1) inserts finger 11 adjacent piezoelectric pulse pickup 12 in inflatable cuff 13. The operator then activates pressure source 17 to increase the pressure in cuff 13 until pressure indicator 20 indicates a pressure of about diastolic pressure. The valve 21 may be opened to reduce the pressure in inflatable cuff 13 to the desired pressure just before and throughout the maneuver. Alternatively, pressure may be increased or decreased. Prior to obtaining measurements of pressure within the arterial system it may be necessary to arterialize the capillary bed in the finger by local application of heat to the arm being tested, or by use of drugs. The finger tube then may act as a Bernoulli chamber and optimizes the ability to obtain measurements of heart mechanical functions. By varying the pressure on the finger the threshold level of force and velocity of the contraction or pumping action of the heart can be evaluated. The waveforms observable with the apparatus reflect the waveform generated by the heart at the aortic root.

The output of the microcomputer is observed for a number of heartbeats at a variety of pressures varying from half diastolic to substantially greater than diastolic, for example, upwards of four times diastolic. By varying the cuff pressure, impedance of blood within the arteries of the fingers may be varied. The output observed is similar to that observed by continuous Doppler of flow velocity in the root of the aorta, just above the aortic valve. By comparing the changes in waveform, contour, and rate which occur with or without interventions (see below), characteristics of shortening and force development of the heart muscle can be obtained so that a determination can be made as to whether heart pumping function is normal or impaired. Similar determinations can be made by increasing or decreasing cuff pressure. Normal patients will show a characteristic response in parameters such as amplitude, slope, width and area of the impulse while patients with impaired hearts will show a different response, and one which is clearly indicative of impairment of the mechanical heart performance of the heart.

The pressure of blood within the systemic arterial system, and the flow of that blood within the system are representative of the kinetic energy developed in the left ventricle of the heart. The root of the aorta is the first point in the circulation to experience the dynamics of ventricular ejection, and the driving force of the systemic arterial circulation begins at this point. The arterial system in the finger receives a fractional, proportionate but characteristic portion of the kinetic energy developed and expressed by the heart. Accordingly, information of diagnostic consequence regarding the quality of the pumping performance of the heart, and especially the left ventricle, can be gained by an analysis of dynamic and kinetic characteristics of the arteries in the fingers. By increasing the pressure of the cuff, changes in the contour of the impulse will occur which will permit normal and abnormal people to be distinguished according to their heart pumping function. The pressure change results in a waveform change in the apparatus of this invention. This change can be observed for normal persons, and alternations observed in abnormal persons will indicate heart dysfunction and will allow quantification of the severity of the abnormality.

Where no pressure is exerted by the cuff on the finger, there is no compression of the arterial system within the finger, and the pressure and flow velocity characteristics of the arterial system where blood flows into the finger are essentially the same as the pressure and flow velocity characteristics within the cuff. Where the finger is compressed, and thus the arterial system within the finger is compressed, the result is the effective cross sectional area of an artery within the finger is smaller than of the artery prior to the compression. Thus, the velocity of flow of the blood increases and the change in impulse sensed by the pickup can be recorded. At a certain pressure blood will be unable to flow through the compressed artery.

The kinetic energy of the blood within the artery in each finger with or without compression is exactly the same at the arterial entry of the finger to the point where the pressure is applied. The kinetic energy meets increasing levels of compression, an the impulse sensed at the finger will reflect the kinetic realities that exist just above the aortic valve, which in turn reflects the kinetic realities within the heart. If the heart is normal, a normal impulse will be observed and a normal response will be observed to each intervention used to test heart pumping function, such as a heart-straining maneuvers (see below); however, if the heart has an abnormality in its pumping function, this abnormality will result in a different impulse contour being observed. For example, if a proportion of the heart muscle has lost its vitality for any reason, the strength of the heartbeat will be decreased, and the changes in force and velocity characteristics of the heartbeat will in turn be altered in a way that can be determined at the finger, or elsewhere, by this system.

The use of simultaneous measurements on three of four fingers with different compression levels will permit gathering of three of four different data points under identical conditions from identical heartbeats, which will aid in the diagnostic impact of this tool.

The method of this invention allows detection of presymptomatic hearts—that is, detection of abnormal hearts despite the absence of physical symptoms in that person, by use of a noninvasive procedure. Previously, such measurements were performed by insertion of a catheter within the arterial system of the heart and measurement of Doppler signals. It has been discovered that such measurements can now be performed with a noninvasive instrument coupled with changing the pressure exerted upon the skin. The simple comparison of the changes in force and velocity characteristics of the heartbeat as determined at the finger by varying pressures at the finger, with or without the use of other heart-straining interventions (see blow) is indicative of the state of the heart's pumping capability.

The above apparatus can be readily modified to provide a plurality of measuring devices which can be attached to a plurality of fingers to allow concurrent measurements at different cuff pressures. This technique is advantageous relative to use of a single finger cuff with varying pressures, since the parameters of a single heart beat at different pressures can be determined free of the influence of any variations between heart beats.

The above apparatus may be supplemented to allow its use when the patient is undergoing heart straining maneuvers, such as the Valsalva maneuver. For example, referring again to FIG. 1, there is shown a mouthpiece 22, preferably replaceable, coupled to hose 24 closed at the far end to define a confined volume and formed with an aperture 23 to release expired air. Pressure transducer 25 is coupled to hose 24 and provides a pressure signal converted by analog to digital converter 26 into digital form representative of the pressure in the confined volume. Microcomputer 15 processes the digital pressure signal to provide a representative signal on computer display 16 representative of the pressure in hose 24.

Figure 8:
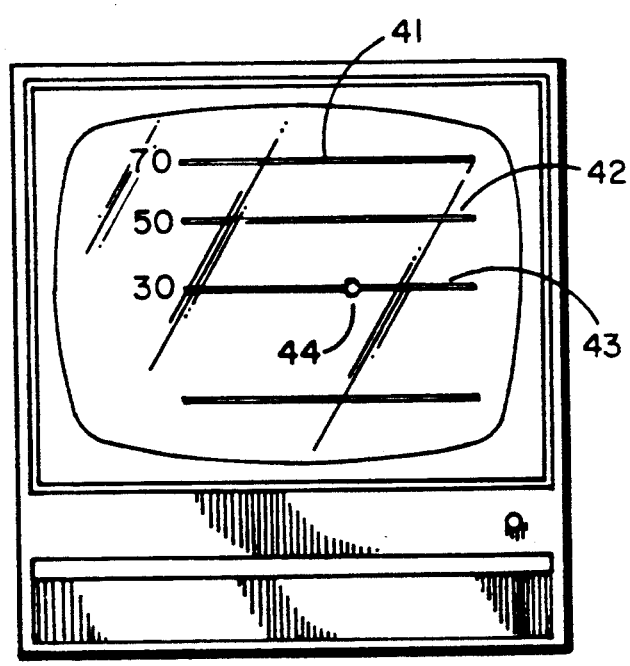
FIG. 8 shows a view of a CRT display for helping a patient control expiration pressure.

Referring to FIG. 8, there is shown a view of a CRT display which may be used for allowing the patient to maintain a preferred pressure range during the test. Upper, intermediate and lower horizontal traces 41, 42 and 43, respectively, may represent pressures of 70 mm, 50 mm and 30 mm, relative to baseline level marked zero, respectively. The patient blows hard enough on mouth piece 22 (FIG. 1) so as to maintain spot 44 on trace 43.

During measurements as above, patient 10 blows into mouth piece 22 to create a pressure in hose 24 of magnitude indicated on computer display that is maintained for preferably 8 to 20 seconds between limits of 30–50 mm of mercury. This strained breathing creates the strain for phases I and II of the Valsalva maneuver (Elisberg, 186 J.A.M.A. 130, 1963). The patient then removes the mouthpiece and relaxes while the recovery and steady state phases of the maneuver follow.

The following discussion concerns measurement of pulse parameters using a cuff pressure at about diastolic pressure. These examples are by way of representation only. Useful data is also obtained by use of greater or lesser cuff pressures in combination with the following procedures, as described above, or without use of heart straining maneuvers.

Figure 2:
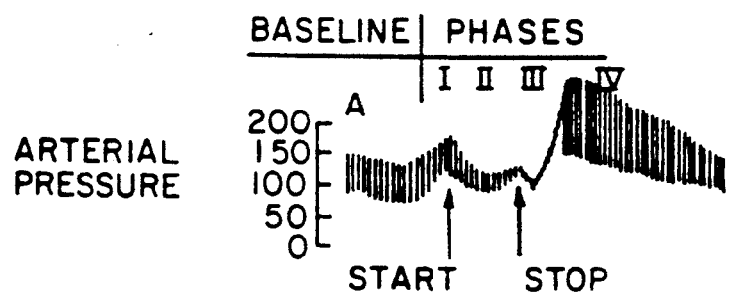
FIG. 2 is a graphical representation of a typical pulse signal just before, during, and following a Valsalva maneuver for a normal or "sinusoidal" response, showing, among other things, a rate increase in phase II over baseline, a rate decrease in phase IV over baseline, and the increase in amplitude in phase IV relative to baseline, referred to as an "over-shoot."

Referring to FIG. 2, there is shown a graphical representation of a pulse waveform just before and during the four phases (I–IV) of a Valsalva maneuver for a normal response showing the changes in arterial pressure as recorded from within the artery. Amplitudes and rates are shown as a function of time during a period of straining between the arrows marked start and stop relative to the amplitude and rate in the control interval just before straining. There is a rise in pressure on straining (phase I) sometimes associated with heart rate slowing; a drop in pressure (phase II) normally accompanied by heart rate increase; a fall below the baseline (phase III) and a post-straining rise (phase IV) normally associated with a heart-rate decrease. The characteristics of the usual normal response of FIG. 2 are set forth in the following Table I relative to the baseline status. O, ↑, ↓ and ↓↓ indicate no change, increase, decrease and large decrease, respectively. An advantage of the invention is that measurements normalized to the prestrain interval for each patient during each test characterize mechanical heart performance.

TABLE I

|  | Phase I | Phase II | Phase III | Phase IV |
|---|---|---|---|---|
| (1) Ht. Rate | 0 or ↓ | ↑ | ↑ | ↓ |
| (2) "dp/dt" | 0 | ↓ or ↑ | ↓ or ↑ | ↑ or 0 |
| (3) ‖ pdt | 0 | ↓ or ↑ | ↓↓ | ↑ |
| (4) Impulse Amplitude | 0 or ↑ | ↓ | ↓↓ | ↑ |
| (5) Peak (systolic) Pressure | ↑ | ↓ | ↓ | ↑ |
| (6) Mean Pressure | ↑ | ↑ or 0 or ↓ | ↓ | ↑ |
| (7) Diastolic Pressure or "Low" Pressure | ↑ | ↑ or 0 or ↓ | ↓ | ↑ |

Figure 3:
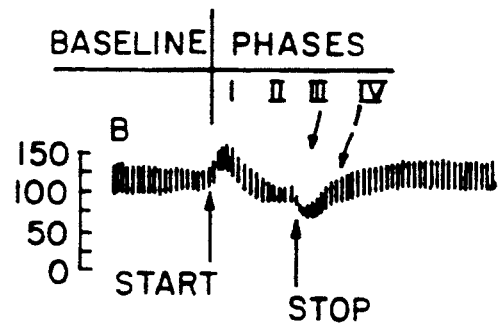
FIG. 3 is a representation the same as FIG. 2 except for an intermediate response with no overshoot in phase IV.

Referring to FIG. 3, there is shown an intermediate abnormal response with no overshoot in phase IV as defined by an increase in "systolic" level of pressure over baseline. The waveform of FIG. 3 relative to the baseline period usually has the characteristics set forth in Table II.

TABLE II

|  | Phase I | Phase II | Phase III | Phase IV |
|---|---|---|---|---|
| (1) Ht. Rate | 0 or ↓ | 0 or ↑ | 0 or ↑ | 0 |
| (2) "dp/dt" | 0 | 0 or ↓ | 0 or ↓ | 0 |
| (3) ‖ pdt | 0 | 0 or ↓ | ↓ | 0 |
| (4) Impulse Amplitude | 0 or ↑ | ↓ | ↓ | 0 |
| (5) Peak (systolic) Pressure | ↑ | ↓ | ↓ | 0 |
| (6) Mean Pressure | ↑ | 0 or ↓ | ↓ | 0 |
| (7) Diastolic Pressure or "Low" Pressure | ↑ | 0 or ↓ | ↓ | 0 |

Figure 4:
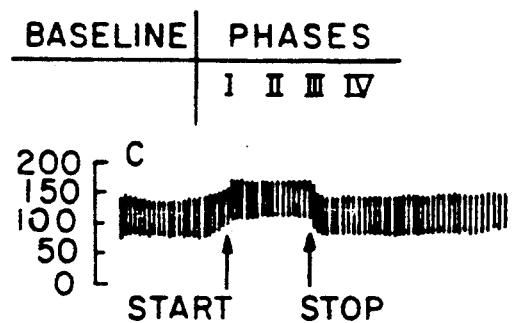
FIG. 4 is a representation similar to FIG. 2 except representative of an abnormal or "square wave" response.

Referring to FIG. 4, there is shown a graphical representation of arterial pressure as a function of time for an abnormal or "square-wave" response to a Valsalva maneuver. The characteristics of this response relative to the base period response is set forth in Table III.

TABLE III

| | Phase I | Phase II | Phase III | Phase IV |
|---|---|---|---|---|
| (1) Ht. Rate | 0 | 0 | 0 | 0 |
| (2) "dp/dt" | 0 | 0 | 0 | 0 |
| (3) ‖ pdt | 0 | 0 | 0 | 0 |
| (4) Impulse Amplitude | 0 | 0 | 0 | 0 |
| (5) Peak (systolic) Pressure | 0 | ↑ | ↑ | 0 |
| (6) Mean Pressure | 0 | ↑ | ↑ | 0 |
| (7) Diastolic Pressure or "Low" Pressure | 0 | ↑ | ↑ | 0 |

Use

The Valsalva maneuver entails the abrupt development and maintenance for a number of seconds of an increase in intrathoracic pressure by forced expiration against a closed glottis or against a closed system as described in this invention. Such an increase in intrathoracic pressure results in a decrease in venous return to the heart, so that filling of the pumping chambers of the heart is normally decreased. Impairment of the filling of the left ventricle (the major pumping chamber of the heart) during this so-called "strain" phase (phase II) results in a prompt fall in blood pressure in the normal individual, followed by an abrupt increase in pulse rate. At termination of "strain" phase in the normal individual, venous return to the heart is abruptly augmented, to a point which generally exceeds the original baseline rate of heart filling phases III and IV. The normal ventricle will increase its work and output in the recovery phase (phase IV) to a level in excess of the "control" level in order to deal with the increase in filling (see FIG. 2). The result is that an "overshoot" occurs in which pulse pressure and blood pressure exceed their levels during the control or baseline level. The body senses this change and responds by reflexly slowing the heart via a sensing mechanism in the arteries and the carotid baroreceptors (phase IV). This normal response has several characteristics that distinguish it from the abnormal response of the patient with ventricular failure:

1) there is usually a fall in blood pressure during the "strain" phase;
2) there is an increase in heart rate toward the end of "strain" phase;
3) there is an "overshoot" shortly after release of the "strain" phase;
4) there is a slowing of heart rate in the course of the "overshoot"; and,
5) there is fairly prompt return to near the baseline level of blood pressure, pulse pressure, and heart rate thereafter.

In the patient with cardiac failure, the physiological response to the Valsalva maneuver is quite different. One characteristic response is called the "square wave" response, shown in FIG. 4. This response involves an increase in blood pressure with the initiation of the strain phase and maintenance of nearly the same blood pressure, pulse pressure and heart rate at this level throughout the "strain" phase. The "recovery" phase which follows the release of the Valsalva maneuver "strain" phase is characterized by a drop in the blood pressure to the baseline level, the absence of any "overshoot" and the absence of recovery period cardiac slowing.

According to this invention, sensitive reproduction and analysis of these differences can be achieved using a noninvasive method, either by the use of a derivative of the impulse generated by the arterial pressure from the pickup or by analysis of changes in peak amplitude and heart rate at various phases, and an integral of that signal and measure of the heart rate, facilitates using this known physiological response as a clinical indicator for cardiac status with apparatus that is compact, relatively inexpensive and relatively easy to operate to produce reliable results. The present invention provides methods and means that enable a practicing physician to detect in his office the presence of occult left ventricular (and/or right ventricular) failure or dysfunction as well as significant abnormalities of heart valves and constrictive and restrictive conditions which affect heart pumping function.

The invention is especially advantageous because the symptoms of left ventricular failure are similar to those associated with other very common illnesses and conditions, some of which may be less threatening. For example, shortness of breath, a very common symptom of heart failure, may be caused by other conditions, e.g., shortness of breath is common among cigarette smokers. With increasing age and some progression of a disease, such as chronic lung disease due to cigarette smoking, the ability to ascertain the presence of underlying heart failure as a contributing factor to a limiting symptom, such as shortness of breath, becomes increasingly difficult and important. The invention helps discriminate between heart failure and other processes which may produce physical symptoms similar to or identical to those caused by heart failure. The invention also helps to demonstrate that the assumed cause of a symptom, e.g., a patient's symptom of shortness of breath, which is otherwise attributed to overweight, or cigarette smoking, is an unsuspected heart failure and is the most important cause of the patient's shortness of breath.

An important advantage of the invention is that it may be used to evaluate the results of treatment for heart conditions. And the ease of use, minimal discomfort to the patient and accessibility to all practitioners enhances health care.

The above described method of use of the apparatus described may be augmented by a variety of techniques to provide data which allows more detailed analysis of potential cardiovascular problems. These techniques involve subjecting the patient to a treatment or activity which affects heart response, as well as to the Valsalva maneuver, and these techniques may be used in combination with or independent of breathing maneuvers such as the Valsalva maneuver. For example, isometric exercise, cardiovascular drugs (such as hydralazine, α-adrenergic and β-adrenergic receptor blockers and amyl nitrate), or inotropic agents (such as adrenalin), immersing an arm in ice water (cold-pressor testing), lying the patient in a supine position, or any position change, exercise tolerance tests, psychological stress tests (e.g., mathematical problem solving) drug treatments (e.g., vasoactive drugs, such as nitroglycerine); balloon angioplasty or coronary artery bypass grafting, may all have effects on heart response. Below are given examples of the use of such techniques and the data which they can generate. However, this invention is not limited to those examples; those skilled in the art will realize that equivalent techniques exist which cause constriction or dilation of arteries or other blood vessels or otherwise after cardiovascular activity so as to represent appropriate "interventions" and thus may be used in this invention.

EXAMPLE 1

In this example isometric exercise (Brown et al. 70 *Circulation* 19, 1984) is used to discern heart or vessel abnormality. The exercise consists of a handgrip exercise, which entails squeezing a gripper tool having a meter indicating the force being exerted on the tool. The patient exerts the maximum force he is able to exert, this force maneuver is then used to estimate a force of about 20-40% maximum. The patient is required to sustain this 20-40% maximum gripping force for 30 seconds to 2 minutes prior and during the Valsalva maneuver, and for about 30 seconds thereafter. The handgrip exercise generally induces a reflex constriction of peripheral arteries that regulate blood pressure, and also of coronary arteries which regulate blood flow through the coronary circulation and myocardium. Thus, this exercise alters the circulation so that it may cause those patients producing apparently normal responses during Valsalva maneuver alone to produce an abnormal response to this maneuver. In other words, a latent abnormality of ventricular function and/or of the coronary arteries, such as coronary artery narrowing, may be unmasked. Such unmasking is possible because a heart which is functioning at a borderline level between normal and abnormal or which has "borderline" coronary artery flow or flow reserve to the heart muscle may not be able to compensate for the extra strain of the handgrip exercise, while it can respond normally to Valsalva maneuver along. For example, handgrip exercise will increase the impedance to ejection of blood from the heart and thereby decrease the rate at which the heart can deliver blood to the circulation because peripheral arteries are constricted and impede blood outflow from the heart. The normal heart will deal with the "strain" in a more efficient manner than the heart with impaired mechanical (pumping) function. The isometric exercise also causes coronary arteries to constrict, and those which are narrowed by disease, although able to supply adequate blood to heart muscle at rest, may narrow to a point at which heart pumping function becomes abnormal, and the abnormality is discernable by this invention. For example, if the patient has arteries which are already 65%-75% narrowed by arteriosclerotic disease, but there are no abnormalities with Valsalva maneuver alone, then isometric exercise or other interventions which cause an additional 10%-15% reflex narrowing which will result in abnormalities of heart function which are detectable by the present invention.

Figure 9:
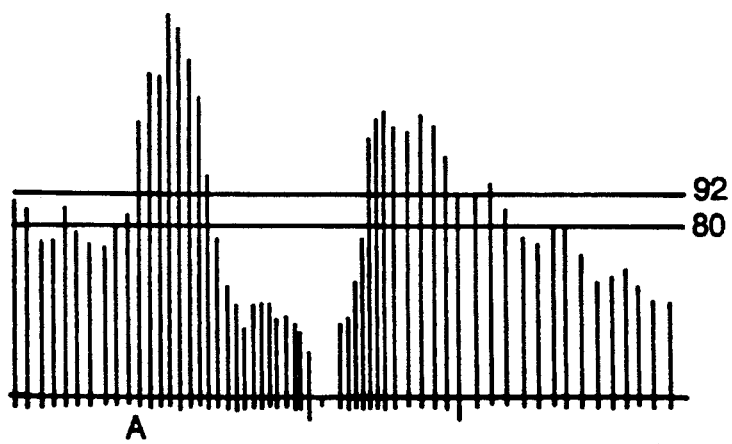
FIG. 9 is a graphical representation of a normal response to a Valsalva maneuver as recorded by the apparatus of this invention, and a table presenting the pulse amplitude or derivative peak and pulse rate values corresponding to those shown on the graph.

Referring to FIG. 9, a normal response to a Valsalva maneuver as enscribed by this invention is shown. The upper two horizontal lines 80, 82 show the baseline amplitude (80) and 20% above baseline (82) of a normal patient. The baseline amplitude will vary between patients and is merely used as a value to compare later responses to the Valsalva maneuver or other interventions. In FIG. 9, the Valsalva maneuver started at point A, and causes an increase (phase I) in blood pressure followed by a rapid decrease (phase II). Further, the rate of heart beat increases during this period, as shown by narrowing of the vertical lines representing impulse amplitudes. At one point the impulse amplitudes is so low that impulses are not detected (phase III). The maneuver is then stopped, and blood pressure increases and overshoots the baseline level (phase IV) and then goes below it. The actual values of impulse amplitudes and pulse rates are given below FIG. 9 in the manner in which they are stored for computer analysis. These values will vary from one patient to another. However, the general shape of the display is a guide to normality of any one patient. A template (an average graphical response) may be readily established for normal responses in order to be able to compare them to abnormal responses. Thus, a computer can be programmed to make comparisons of any set of people which have been ranked according to any parameters, which are thought to affect the observed response. For example, if a normal rate response increases by 30-40 % or decreases by about 10-20%, the finding that an individual tested fell outside this range would be an indication of a problem. Similarly, amplitude, changes in phase IV of less than 20% over baseline would be indicative of a problem. Ratios and other formulae involving these parameters can be calculated and used to produce an index which is suitable for diagnosis of particular problems. In addition, other factors, such as the time to detect certain responses, e.g., the recovery time from Valsalva maneuver, can be included in this index.

Figure 10A:
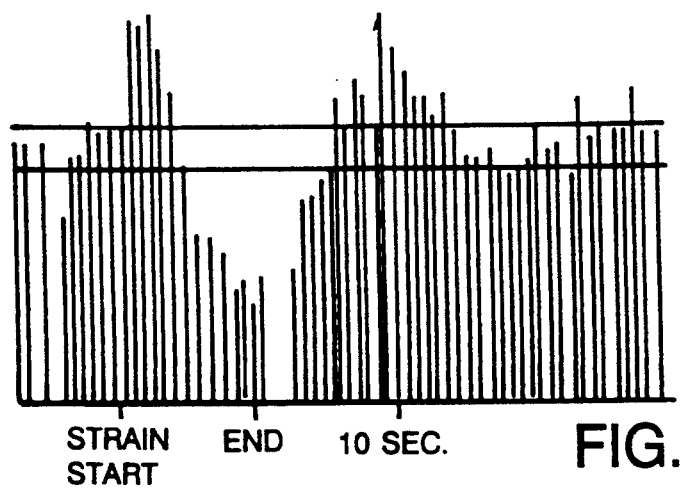
FIGS. 10-17 are graphical representations of responses to Valsalva maneuvers and various interventions as enscribed by the invention. Specifically.
Figure 10B:
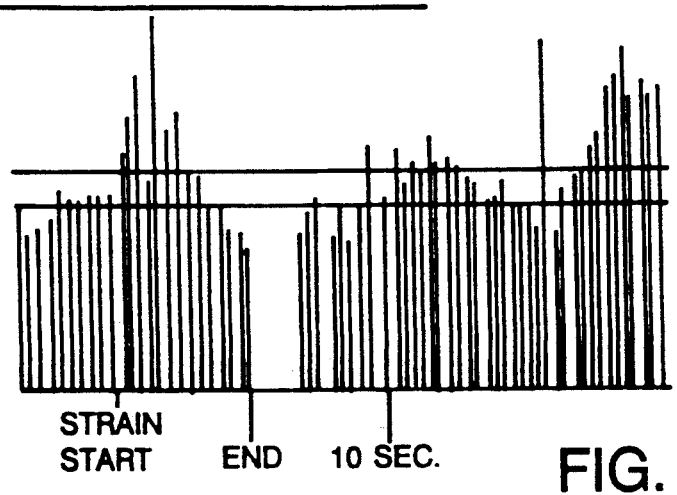
Figure 10C:
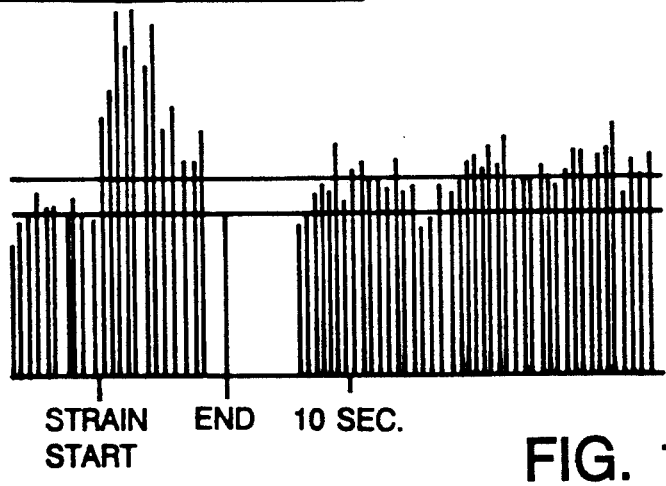

Referring to FIG. 10A, in this patient phases I-III of the display are normal, whereas phase IV has a blunted overshoot. Further, the heart rate is relatively unchanged throughout the maneuver, which is a sign of abnormality. Thus this response in abnormal indicating that this patient may have a borderline heart response. In order to confirm this analysis interventions were performed. In FIG. 10B handgrip exercise was performed during the Valsalva maneuver. This reduced the overshoot in phase IV. As an extra intervention the patient was then caused to move from the sitting to the supine position. This maneuver increases the rate of blood flow to the heart and thus increases stress on the heart. Referring to FIG. 10C, the display obtained with a supine patient obliterated the overshoot and produced a square wave. This indicates that blood volume in the lungs is excessive, and the heart is unable to pump blood from the pulmonary veins to the aorta at a fast enough rate. This is evidence of pulmonary congestion, i.e., heart failure. Further, phase I and II now appear as a square wave, which is further evidence of heart failure.

Thus, in this patient intervention with handgrip exercise and supine positioning reveals that the heart is acting at a borderline level and that the patient needs treatment of some sort. Without such intervention the patient would have been released and asked to return in a few months for a repeat analysis. During this period the patient may have died from the undetected heart failure. The above method, of providing a second intervention, unmasks clinically inapparent increases in left ventricular filling pressure, and allows diagnosis of borderline heart problems.

EXAMPLE 2

Figure 11A:
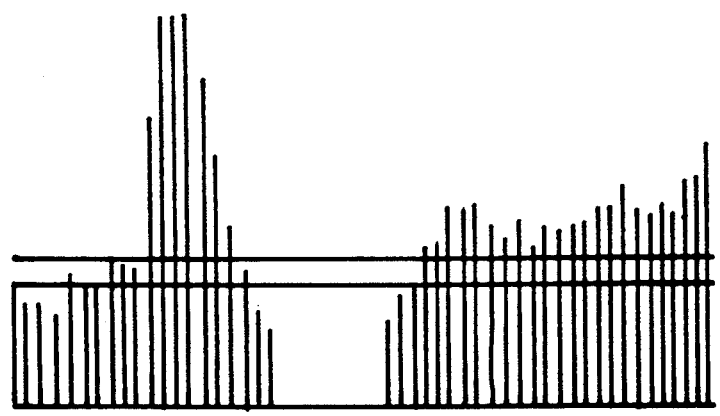
Figure 11B:
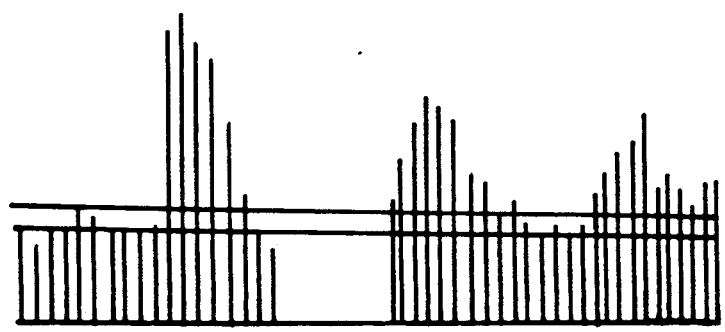
Figure 11C:
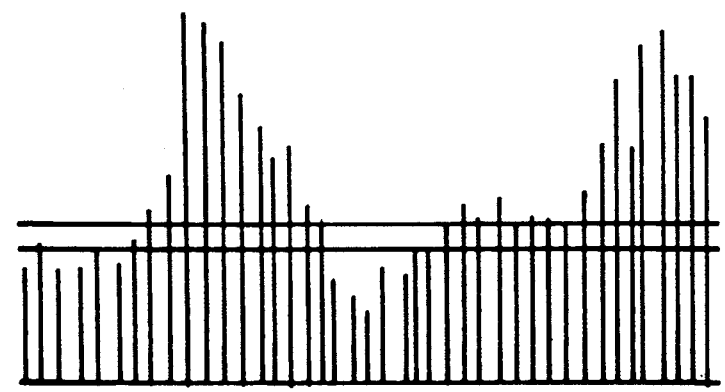
Figure 11D:
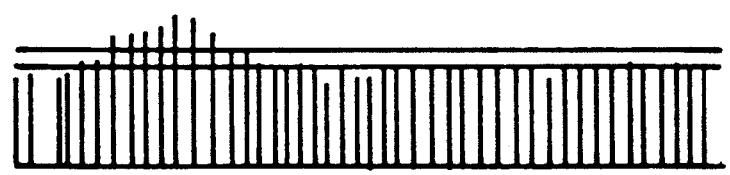

Referring to FIG. 11A, this patient's response to a Valsalva maneuver shows an abnormal overshoot (phase IV). In FIG. 11B, this maneuver was repeated and shows an almost normal response. However, when a handgrip exercise was included, the display, shown in FIG. 11C, shows a blunted overshoot. Finally, when the patient is supine the display, shown in FIG. 11D, is a complete square wave, demonstrating heart failure.

Thus, once again a borderline abnormal display in a patient was shown to reflect an underlying chronic heart failure.

EXAMPLE 3

Figure 12A:
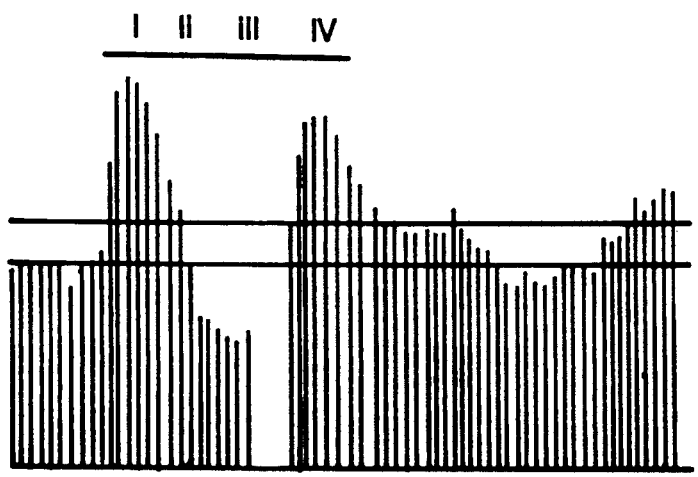
Figure 12B:
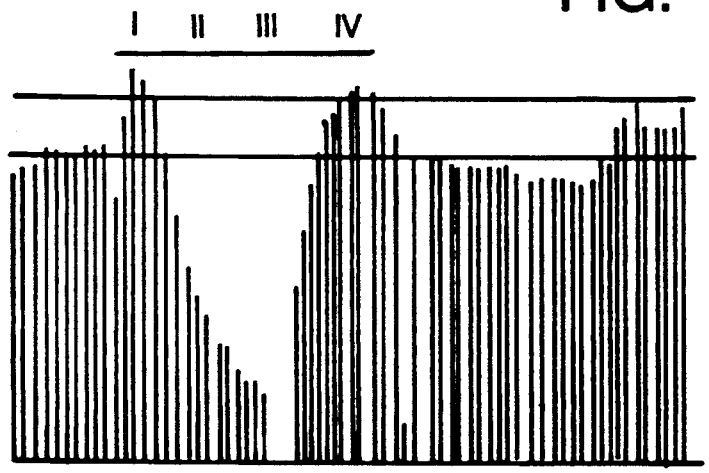
Figure 12C:
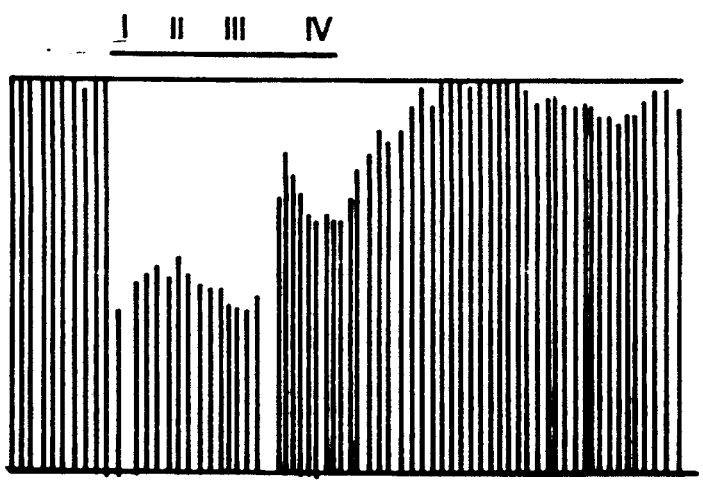

Referring to FIG. 12A, the response to Valsalva maneuver alone is normal, except for a phase IV bradycardia (heart slowing). This response changes drastically when the patient is caused to elevate his legs in the supine position. This intervention is more stressful than simply placing the patient supine. As shown in FIG. 12B, this results in flattening of the overshoot. In FIG. 12C is shown the result of two interventions, where the legs are raised as above, and a handgrip exercise is performed. Now the display is square wave, with failure to recover to baseline pressure. This indicates a serious impairment of heart-pumping function which was not otherwise apparent in this patient.

EXAMPLE 4

Figure 13A:
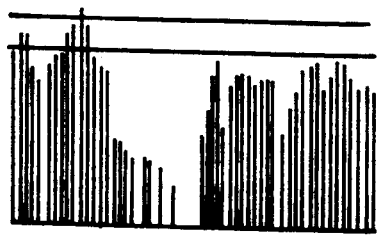
Figure 13B:
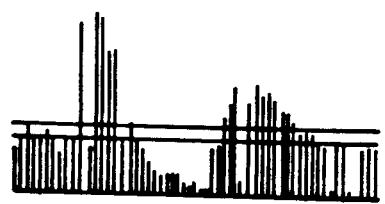

Referring to FIG. 13A, the patient has an abnormal response to Valsalva maneuver showing absent overshoot. After treatment for 5 days with verapamil the patient's severe exertional dyspnea symptoms improved and the phase IV overshoot became normal (FIG. 13B). Thus, a drug treatment can be followed using this apparatus to discover whether the underlying problems giving rise to heart failure are being overcome.

EXAMPLE 5

Figure 14A:
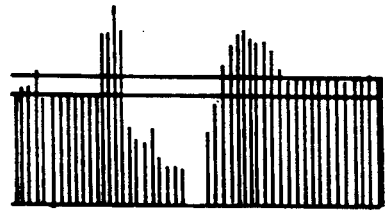
Figure 14B:
Figure 14C:

Referring to FIG. 14, the patient showed a modest overshoot response (FIG. 14A) which is lost when handgrip exercise is performed (FIG. 14B), and becomes a square wave when the patient is supine (FIG. 14C). This patient may be suffering from a decline in aortic blood flow acceleration. This analysis can be readily confirmed by Doppler analysis. Thus, a patient with a borderline normal response can be analyzed by interventions to discover the underlying problem in the heart; this analysis can then be confirmed by other procedures.

EXAMPLE 6

Figure 15A:
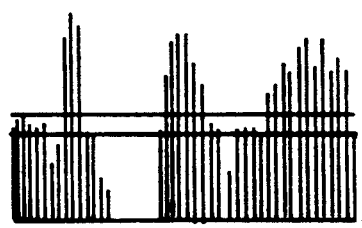
Figure 15B:
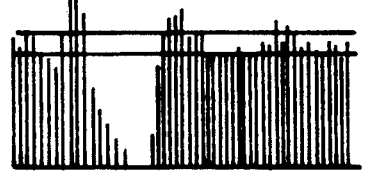
Figure 15C:
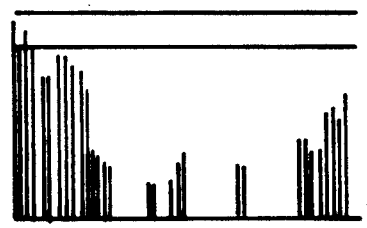
Figure 16A:
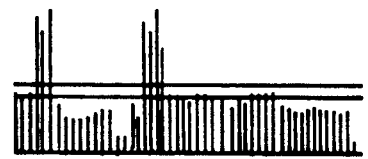
Figure 16B:
Figure 16C:
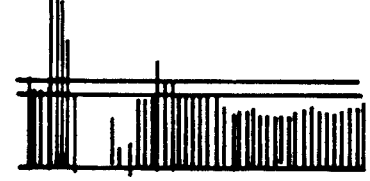
Figure 16D:
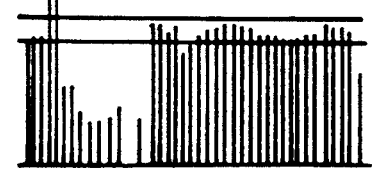

Referring to FIG. 15, this patient has a normal Valsalva response (FIG. 15A), which deteriorates when the Valsalva maneuver is repeated (FIG. 15B) and worsens with handgrip exercise (FIG. 15C). This patient was one year post anterior myocardial infection; and now appears to have severe left ventricle dysfunction. Thus, as in example 4, clinical treatment can be followed using the above interventions. Such interventions are noninvasive and more preferable to the alternative invasive procedures.

EXAMPLE 7

Referring to FIG. 16, a severe three vessel coronary artery disease was detected by repeated Valsalva maneuvers (FIGS. 16 A-D) where the display goes from normal to square wave.

EXAMPLE 8

Figure 17A:
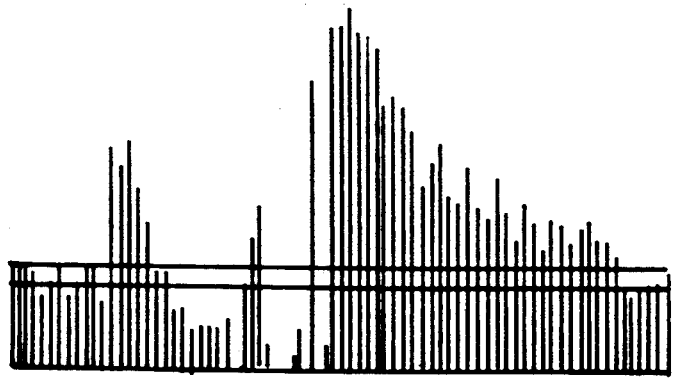
Figure 17B:
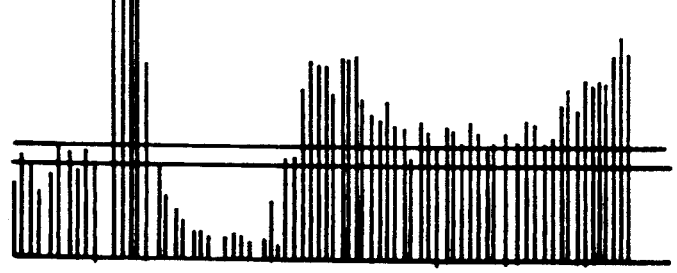
Figure 17C:
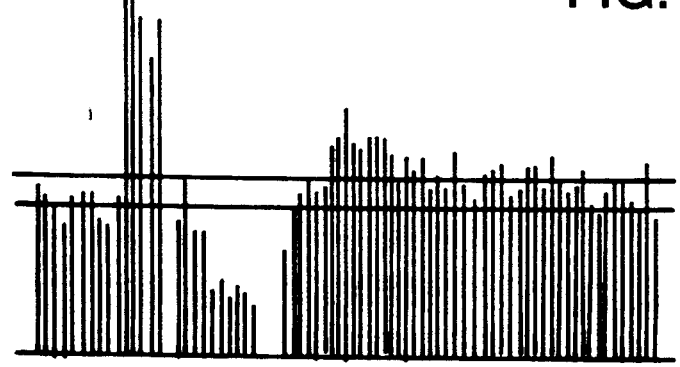
Figure 17D:
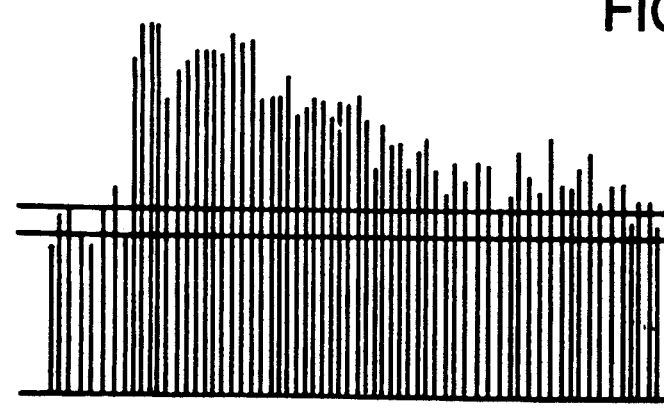

Referring to FIG. 17, this patient shows a response which is strongly suggestive of normal ventricular function (FIG. 17A). However, repeated Valsalva (FIG. 17B), followed immediately by handgrip exercise (FIG. 17C) and then with the patient supine (FIG. 17D) shows a square wave response, indicating heart failure.

The above examples demonstrate that interventions can be used to uncover a previously inapparent impairment (a latent impairment) in heart muscle pumping function, either by imposing a modest increase in load upon the heart muscle, or by altering the filling and emptying of the heart. Latent abnormalities or improvements from drugs or other treatments can be detected and monitored. Detected improvements will point toward therapeutically effective interventions. This invention provides a convenient test to check on patients with borderline or even normal appearing responses to Valsalva maneuver. Rather than risk a patient dying between two test periods, this test will detect a patient suffering from chronic heart failure but having no symptoms. Thus, for example, the invention allows ready determination of whether a patient having shortness of breath, but a normal response to Valsalva maneuver, has heart failure or merely a cold.

Once an abnormality is detected the intervention performed can be administration of a drug to determine whether it cures the defect (see example 4). Thus, if the defect is caused by the heart arteries constricting too much, then administration of a suitable drug may alleviate the defect, and thus produce a normal Valsalva response, but if the defect is caused by a physical blockage in a defective artery, then such a drug will have little, if any, effect on the Valsalva response. Similarly, the intervention could entail performing balloon angioplasty to remove a known physical defect in an artery. The response to a Valsalva maneuver should improve if this arterial defect was the cause of the observed defective response.

Although the maneuvers used to detect heart defects are generally relatively comfortable for the patient to perform, they still allow detection of subtle heart failure. People may even have chronic heart failure (shown as a square wave response, see example 1) during these interventions, and show no symptoms of distress. Suitable treatment for such heart failure can then be monitored using the apparatus of this invention and supplying the patient with drugs, such as a nitrate, calcium channel blocker or angiotensin converting enzyme inhibitor to see if any of these prevent formation of a square wave. Thus, the immediate effect of a drug can be discerned. Similarly, a patient can be followed after a successful angioplasty to ensure that the treated vessel does not restenose. This invention is a much less intrusive method than the recatherization and angiography normally used. In this way patients can be regularly followed by noninvasive techniques, and deterioration in blood flow readily detected before symptoms recognizable without the invention.

The apparatus of this invention is also useful for estimation of ejection fraction (EF) of a heart; that is, the percentage of blood in the heart that a heart pumps out at each beat. Normally this is above 50%, usually 60-65%. EF is a predictive and prognostic indicator of heart disease. When EF is 20-35% the person may have chronic heart failure. If it is between 10-20% the heart is seriously impaired. The responses to Valsalva maneuver shown above are predictive of EF. EF is also estimated by looking at the rate response; lack of change in this response is predictive of a low EF value. Such analysis is indicative that the patient needs a follow up examination to determine more precisely what problems are present with his heart and vessels. Thus, the method of this invention serves as a preliminary screen.

Patients with normal EFs may still have abnormal heart failure. For example, one patient having an EF of 58% had no overshoot in phase IV; this abnormality indicates an abnormality of heart function. Thus, this method detects defects in people who need treatment which are otherwise undetected by measuring EF by other methods.

The rate changes during the Valsalva maneuver are also useful to determine whether there is a technical problem in measurement. For example, if no overshoot is observed but the rate slows, then an error in measurement must have occurred.

Although the apparatus produces an amplitude which can be related to pressure, enclosing the finger in a stiff tube provides information which appears to represent flow velocity of the blood. Flow velocity is a good measure of heart function because changes occur earlier than pressure changes, it is sensitive to modest ischemia, and can be predictive of problems. Measurements can be made indicative of heart failure without having to produce painful symptoms in the patient. This method can be used to predict certain hemodynamic measurements, which are described by Gorlin.

Further improvements to the above apparatus include providing means for automatically altering the pressure exerted by the cuff in response to pressure changes in the arterial system, for example, when heart straining maneuvers are used. This feature allows more effective characterization of the force-pressure development and shortening-ejection realities of the left ventricle. Adaptation of the apparatus to compute changes in the contour, rise time, maximum rate of rise, time to peak, total amplitude, duration, integrated area under the inscribed pulse, and integrated area divided by time (ejection parameter) allows other diagnostic comparisons of normal and abnormal hearts.

Other uses of this invention include determination of deterioration of ventricular function in acute myocardial infarction, and thus define when invasive hemodynamic monitoring or other aggressive interventions should be initiated; identification of significant valvular disease in individuals with heart murmurs which are not known to be significant; identification of otherwise undetected valvular disease; identification of dynamic contribution to coronary artery disease using cold-pressor testing; identification of abnormal cardiovascular reflex responses, such as neurologic problems or hypotension, in patients with abnormal rate responses; and demonstration of a positive hemodynamic impact of calcium channel blockers in idiopathic hypertrophic subaortic stenosis.

The use of the above apparatus and method in conjunction with an electrocardiogram, a pulmonary function testing capability and oximetry allows important diagnostic information to be obtained. This combination allows diagnosis of disease that may otherwise be missed, and prevents unnecessary treatment of disease not caused by heart failure, or heart muscle deficiency. The combination provides more information than each of the individual methods alone.

Figure 18:
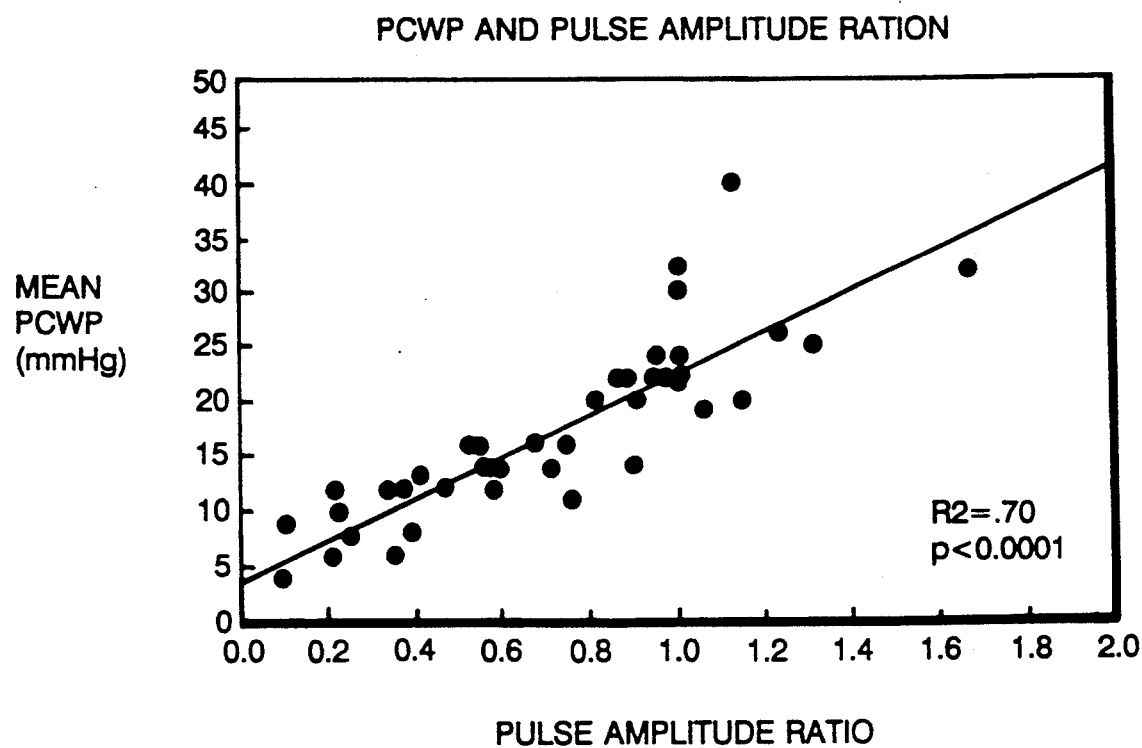
FIG. 18 shows the relationship between pulse amplitude ratio determined noninvasively according to the invention and pulmonary capillary wedge pressure (PCWP)

Referring to FIG. 18, there is shown a graphical representation of the relationship between pulse-amplitude ratio (PAR) measured noninvasively according to the invention and pulmonary-capillary wedge pressure (PCWP). Each dot corresponds to the PAR measured noninvasively according to the invention and the PCWP measured invasively conventionally. The line is the best fit among these measured points using standard least-squares linear regression analysis. The base-line measurements indicated that the PAR predicted the measured PCWP over a range of values from 4 mm Hg to 32 mm Hg with good accuracy. The details of the methods and results of carefully conducted tests are described in an article entitled A NONINVASIVE METHOD OF PREDICTING PULMONARY-CAPILLARY WEDGE PRESSURE by Kevin M. McIntyre, M.D., Joseph A. Vita, M.D., Costas T. Lambrew, M.D., Jonathan Freeman, M.D., Sc.D., and Josephh Loscalzo, M.D., PH.D., THE NEW ENGLAND JOURNAL OF MEDICINE, Vol. 327, No. 24, Pp. 1715-20 (Dec. 10, 1992) incorporated by reference herein. An earlier draft of this article appeared as an appendix in the aforesaid parent application.

The invention is helpful in evaluating dehydration, a very common condition among the elderly. The invention may be used for predicting levels of a hormone called atrial natriuretic peptide, which is known to increase in the elderly and to be strongly associated with central cardiac filling pressures, of which PCWP is one, and with the future development of heart failure. The invention may also be used to reflect progressive increases in fluid retention and aerial natriuretic peptide when a salt-retaining hormone (Florinef) was administered to demonstrate the potential danger to the elderly patients of a decrease in their ability to eliminate excess salt, a condition associated with elevation of PCWP into the heart failure range in susceptible patients.

Figure 19A:
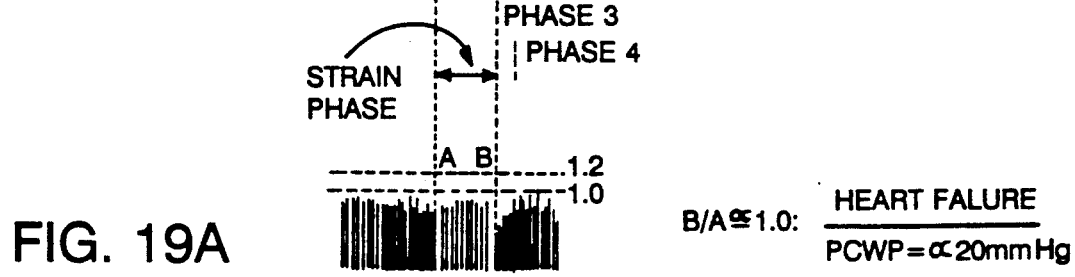
FIGS. 19A, 19B, 19C and 19D show patient conditions involving the use of the invention for detecting a state of dehydration.
Figure 19B:
Figure 19C:
Figure 19D:
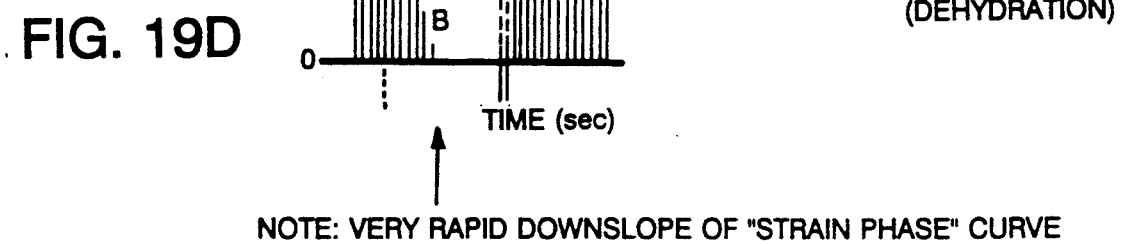

Referring to FIG. 19A, there is shown a graphical representation of a response to a Valsalva maneuver indicating a patient condition of volume over-loaded, a very common condition among the elderly. The ratio of B amplitude to A amplitude (B/A) shows a pulse amplitude ration (PAR) about 1.0 corresponding to a PCWP of 20 mm Hg, significantly increased. Referring to FIG. 19B, there is shown a graphical representation of a response with the ratio of B/A reduced, but still corresponding to an abnormally high PCWP. Referring to FIG. 19C, there is shown a graphical representation of a response with the ratio B/A normal and corresponding to a relatively "normovolemic" state of the patient. Referring to FIG. 19D, there is shown a graphical representation of a response of a patient having hypovolemia or dehydration exhibiting a significantly more abrupt decline in the impulse amplitude through the course of the strain phase from A to B.

It is believed that this rate of change will increase (declining more sharply) with increasingly severe dehydration (assuming reasonably normal cardiovascular function); the time-to-loss of recorded impulse will decrease; the rate at which heart rate will increase, will increase; and the heart rate peak (and peak change from baseline) will increase. It may be advantageous to also perform EKG monitoring to record the heart rate changes accurately because some impulses may be lost as the recorded pulse amplitude approaches zero as seen in FIG. 19D to the right of B.

Figure 20A:
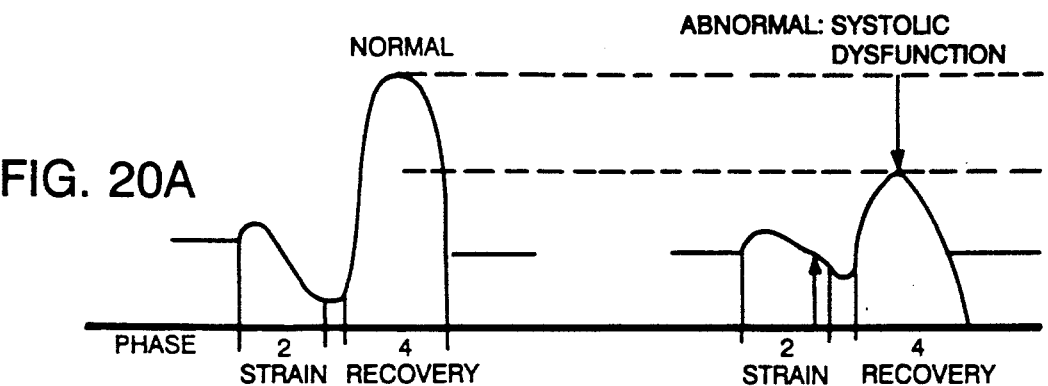
FIGS. 20A, 20B and 20C are diagrammatic representations of normal responses beside abnormal responses indicating systolic dysfunction, diastolic dysfunction and combinations thereof, respectively.
Figure 20B:
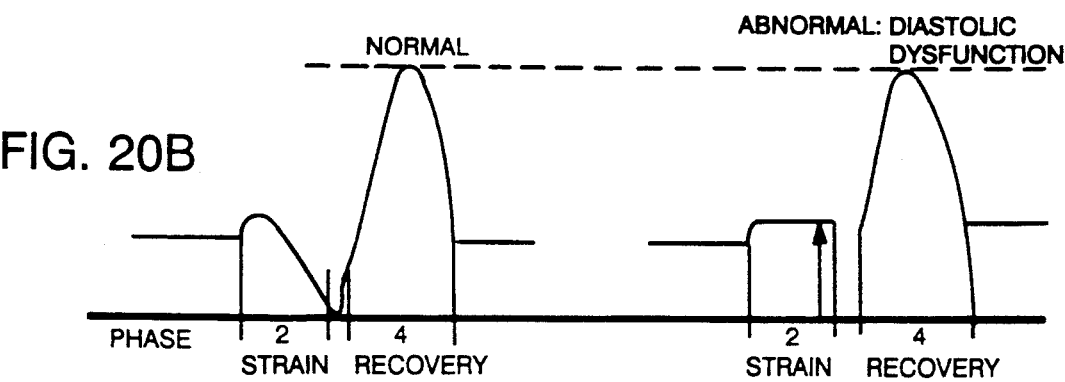
Figure 20C:
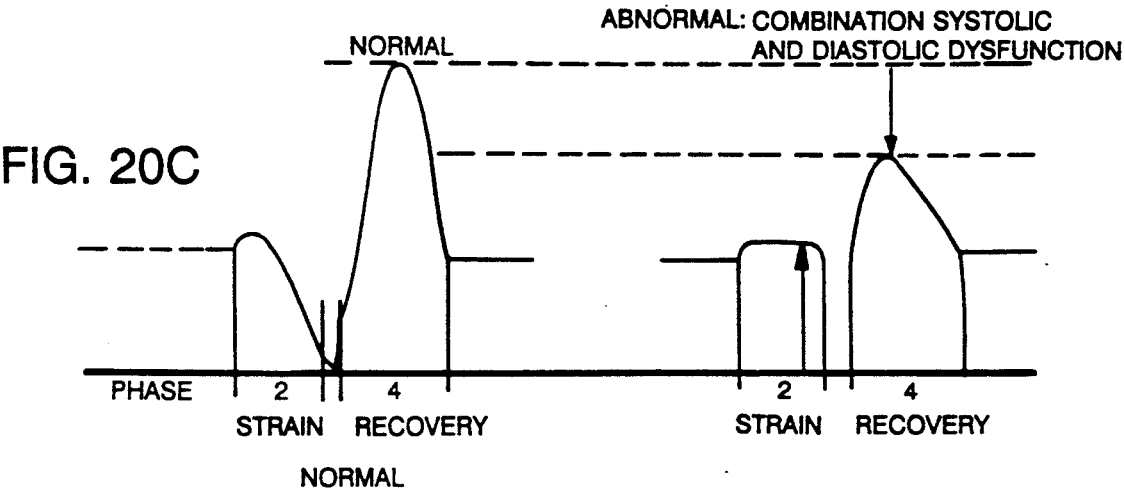

Referring to FIGS. 20A, 20B and 20C, there are shown schematic representations of envelopes in strain and recovery phases helpful in identifying systolic dysfunction, diastolic dysfunction and a combination of systolic and diastolic dysfunction. The envelope for the normal response is shown at the left. The abnormal responses are shown at the right. FIG. 20A shows that for systolic dysfunction, there is shallower slope of decline in the strain phase than normal and significant reduction in amplitude during the recovery phase. FIG.

20B shows that for diastolic dysfunction, the envelope amplitude during the strain phase is essentially constant. FIG. 20C shows that for a combination of systolic and diastolic dysfunction, there is both substantially uniform amplitude during the strain phase and reduced amplitude during the recovery phase.

There has been described novel apparatus and techniques for facilitating evaluating the pumping condition of the heart. It is evident that those skilled in the art may now make numerous uses and modifications of and departures from the specific apparatus and techniques described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A method of evaluating the mechanical condition of a heart which method includes the steps of,
   noninvasively providing a pulse signal representative of arterial pulsation by placing pressure sensitive transducing means for providing an electrical signal representative of pressure in contact with the skin of a patient while applying pressure at least in part through the pressure sensitive transducing means to adjacent skin at a controlled pressure within the range of at least just above the diastolic pressure of said patient and a pressure of substantially half of said diastolic pressure,
   and detecting said pulse signal.

2. A method of evaluating the mechanical condition of a heart in accordance with claim 1 wherein said method includes the steps of,
   noninvasively providing said pulse signal representative of arterial pulsation by placing said pressure sensitive transducing means for providing an electrical signal representative of pressure in contact with the skin of a patient while applying pressure at least in part through the pressure sensitive transducing means to adjacent skin at a controlled pressure within the range of just above diastolic pressure to significantly greater than diastolic pressure, and detecting said pulse signal.

3. The method of claim 2, wherein said pressure range extends to four times diastolic.

4. The method of claim 2 further comprising subjecting said patient to a heart straining maneuver,
   and detecting the change in said pulse signal during and after said maneuver relative to said pulse signal before said maneuver.

5. A method of evaluating the mechanical condition of a heart in accordance with claim 4 wherein said patient expires into a confined volume to develop expiration pressure therein,
   providing an expiration signal representative of said expiration pressure,
   and observing an indication of the expiration pressure signal while maintaining said expiration pressure within predetermined limits for at least a predetermined interval.

6. A method in accordance with claim 4 wherein said step of placing pressure sensitive transducing means in contact with the skin of said patient includes the step of placing a digit of said patient into a cup-shaped container in contact with said pressure sensitive transducing means and a surrounding inflatable cuff, and applying said controlled pressure to the skin of said digit with said inflatable cuff.

7. A method of evaluating the mechanical condition of a heart in accordance with claim 4 wherein the step of detecting the change in said pulse signal after said maneuver relative to said pulse signal before said maneuver includes detecting the change in rate and amplitude.

8. A method of evaluating the mechanical condition of a heart in accordance with claim 4 wherein the step of detecting the change in said pulse signal after said maneuver relative to said pulse signal during said base period includes detecting changes in heart rate, the time derivative of a signal related to blood pressure, the time integral of said signal related to blood pressure, the impulse amplitude of said pulse signal, the peak systolic pressure represented by said pulse signal, and the mean pressure represented by said pulse signal.

9. A method of evaluating the mechanical condition of a heart in accordance with claim 4 and further including the step of providing a display of the peak pressures represented by a sequence of pulse signals and the inverse of the time interval between consecutive pulse signals corresponding substantially to instantaneous heart rate.

10. The method of claim 1 comprising noninvasively providing a plurality of pressure sensitive transducing means in contact with separate portions of the skin of the patient while applying a plurality of different pressures to the skin adjacent each said means within said range.

11. Apparatus for evaluating the mechanical condition of a heart of a patient having skin, comprising,
   pressure sensitive transducing means responsive to arterial pulsation for providing a pulse signal representative of arterial pulsation,
   pressure applying means for applying controlled pressure through means including said pressure sensitive transducing means to the patient skin and maintaining said controlled pressure within the range of significantly above the diastolic pressure of said patient and a pressure substantially half said diastolic pressure,
   and means for detecting the change in said pulse signal during and after a heart straining maneuver reactive to said pulse signal just before said heart straining maneuver.

12. Apparatus in accordance with claim 11 and further comprising,
   container means carrying said pressure sensitive transducing means and inflatable means for applying pressure to the patient skin through means including said pressure sensitive transducing means,
   and means for selectively inflating said inflatable means to said controlled pressure just before, during and at least shortly after said heart straining maneuver.

13. The apparatus of claim 11 comprising a plurality of said transducing means and a plurality of said applying means.

14. A method of evaluating the mechanical condition of a heart in a patient which method includes the steps of,
   noninvasively providing a pulse signal representative of arterial pulsation by placing transducing means for providing an electrical signal representative of said arterial pulsation closely adjacent to the skin of said patient, subjecting said patient to a heart-straining manoeuver to provide an arterial pulse contour square wave signal during said heart-straining manoeuver having an early strain phase amplitude at the beginning of said heart-straining manoeuver and a late strain phase amplitude at the end of said heart-straining manoeuver, and providing an indication of the ratio of said late strain phase amplitude to said early strain phase amplitude which ratio is representative of the mechanical condition of the heart of said patient.

15. A method in accordance with claim 14 wherein said patient has a pulmonary capillary wedge pressure and further including the step of noninvasively providing an indication of the relationship between said ratio and the pulmonary capillary wedge pressure of said patient.

16. A method in accordance with claim 14 and further including the step of noninvasively providing an indication of the state of hydration of said patient.

17. A method of evaluating the mechanical condition of a heart in a patient which method includes the steps of, noninvasively providing a pulse signal representative of arterial pulsation by placing transducing means sufficiently close to the skin of said patient to provide an electrical signal representative of said arterial pulsation, subjecting said patient to a heart-straining maneuver to provide an arterial pulse contour square wave signal during said heart-straining manoeuver having an early strain phase amplitude at the beginning of said heart-straining maneuver and a late strain phase amplitude at the end of said heart-straining maneuver, and providing an indication of the ratio of said late strain phase amplitude to said early strain amplitude which ratio is representative of the mechanical condition of the heart of said patient.

18. A method in accordance with claim 17 wherein said patient has a pulmonary capillary wedge pressure and further including the step of noninvasively providing an indication of the relationship between said ratio and the pulmonary capillary wedge pressure of said patient.

* * * * *

UNITED STATES PATENT AND TRADEMARK OFFICE
CERTIFICATE OF CORRECTION

PATENT NO. : 5,291,895
DATED : March 8, 1994
INVENTOR(S) : Kevin M. McIntyre

It is certified that error appears in the above-indentified patent and that said Letters Patent is hereby corrected as shown below:

Title page, "18" claims," should read --20 claims,--.

Column 1, line 10, "7/563,869" should read --07/563,869--.

Column 2, line 66, "B-adrenergic" should read --β-adrenergic--.

Column 5, line 19, "step" should read --stem--.

Line 21, "step" should read --stem--.

Column 6, line 57, "The" should read --This--.

Line 58, "an" should read --and--.

Column 7, line 6, "of" second occurrence, should read --or--.

Line 8, "of" second occurrence, should read --or--.

Column 11, line 35, "along" should read --alone--.

Column 15, line 2, "failure" should read --function--.

Column 16, lines 10-11, "Josephh" should read --Joseph--.

Column 18, line 47, "reactive" should read --relative--.

UNITED STATES PATENT AND TRADEMARK OFFICE
CERTIFICATE OF CORRECTION

PATENT NO. : 5,291,895

DATED : March 8, 1994

INVENTOR(S) : Kevin M. McIntyre

It is certified that error appears in the above-identified patent and that said Letters Patent is hereby corrected as shown below:

Column 20, after claim 18 add--

19. A method in accordance with claim 18 and further including administering a salt-retaining hormone to said patient so that said ratio is representative of the ability of said patient to eliminate excess salt.

20. A method in accordance with claim 17 and further including the step of noninvasively providing an indication of the state of hydration of said patient.--.

Signed and Sealed this

Nineteenth Day of March, 1996

Attest:

BRUCE LEHMAN

Attesting Officer

Commissioner of Patents and Trademarks